United States Patent
Nitta et al.

(10) Patent No.: US 9,408,991 B2
(45) Date of Patent: Aug. 9, 2016

(54) PUMP UNIT AND BREATHING ASSISTANCE DEVICE

(75) Inventors: Kazufuku Nitta, Kawaguchi (JP); Jun Nitta, Kawaguchi (JP)

(73) Assignee: Metran Co. Ltd., Saitama (JP)

( * ) Notice: Subject to any disclaimer, the term of this patent is extended or adjusted under 35 U.S.C. 154(b) by 981 days.

(21) Appl. No.: 13/345,860

(22) Filed: Jan. 9, 2012

(65) Prior Publication Data

US 2012/0304993 A1    Dec. 6, 2012

(30) Foreign Application Priority Data

May 31, 2011   (JP) ................. 2011-121270

(51) Int. Cl.
*A61M 16/00* (2006.01)
*F04B 19/00* (2006.01)
*F04B 43/04* (2006.01)
*F04B 45/04* (2006.01)
(Continued)

(52) U.S. Cl.
CPC .......... *A61M 16/0072* (2013.01); *F04B 19/006* (2013.01); *F04B 43/043* (2013.01); *F04B 43/046* (2013.01); *F04B 45/043* (2013.01); *F04B 45/047* (2013.01); *A61M 16/12* (2013.01); *A61M 2016/0027* (2013.01); *A61M 2016/0039* (2013.01); *A61M 2205/3375* (2013.01); *A61M 2205/502* (2013.01)

(58) Field of Classification Search
CPC .... F04B 43/043; F04B 19/006; F04B 45/043; F04B 45/047; F04B 43/046; A61M 16/0057; A61M 16/006
USPC ............... 128/204.18; 417/413.1, 322, 413.2, 417/413.3, 62, 505
See application file for complete search history.

(56) References Cited

U.S. PATENT DOCUMENTS 5,836,750 A * 11/1998 Cabuz ........................... 417/322
5,942,443 A * 8/1999 Parce et al. ..................... 506/39
(Continued)

FOREIGN PATENT DOCUMENTS

| EP | 1655052 A3 | 7/2006 |
| JP | 2006130320 A | 5/2006 |
| WO | 2008069266 A1 | 6/2008 |

OTHER PUBLICATIONS

Office Action dated Jul. 3, 2014, issued in co-pending corresponding Chinese Patent Application No. 201210018477.3.

*Primary Examiner* — Alexander Comley
(74) *Attorney, Agent, or Firm* — Porzio, Bromberg & Newman, P.C.

(57) ABSTRACT

A pump unit can achieve significant size reduction while maintaining the performance thereof. Micropumps are arranged in a lattice pattern with rows and columns, and a discharge port of at least a micropump arranged in the most downstream row is directly connected to an integrated discharge port. The pump unit further includes: a discharge direct-connection mechanism for connecting respective discharge ports of a plurality of micropumps in a middle row directly to the integrated discharge port; an intake direct-connection mechanism for connecting respective intake ports of the micropumps directly to a fluid to be supplied first; a series-connection mechanism for connecting a discharge port of a micropump in an upstream row directly to an intake port of a micropump in a downstream row; and a controller for controlling the discharge direct-connection mechanism, the intake direct-connection mechanism, and the series-connection mechanism.

8 Claims, 18 Drawing Sheets

(51) Int. Cl.
*F04B 45/047* (2006.01)
*A61M 16/12* (2006.01)

(56) References Cited

U.S. PATENT DOCUMENTS

| | | | |
|---|---|---|---|
| 5,950,621 A * | 9/1999 | Klockseth et al. | 128/204.26 |
| 6,106,245 A * | 8/2000 | Cabuz | 417/322 |
| 6,179,586 B1 * | 1/2001 | Herb et al. | 417/480 |
| 6,568,286 B1 * | 5/2003 | Cabuz | 73/863.33 |
| 6,892,525 B2 * | 5/2005 | Guiheen et al. | 60/200.1 |
| 7,118,910 B2 * | 10/2006 | Unger et al. | 435/288.5 |
| 7,476,363 B2 * | 1/2009 | Unger et al. | 422/504 |
| 2004/0234401 A1 * | 11/2004 | Banister | 417/474 |
| 2005/0129581 A1 * | 6/2005 | McBride et al. | 422/100 |
| 2006/0096596 A1 * | 5/2006 | Occhialini et al. | 128/204.18 |
| 2009/0232682 A1 * | 9/2009 | Hirata et al. | 417/413.2 |
| 2009/0232683 A1 | 9/2009 | Hirata et al. | |

* cited by examiner (A)

(B)

PUMP UNIT AND BREATHING ASSISTANCE DEVICE

CROSS-REFERENCE TO RELATED APPLICATION

This application claims priority to Japanese Patent Application No. 2011-121270 filed on May 31, 2011, hereby incorporated in its entirety by reference into this application.

BACKGROUND OF THE INVENTION

1. Field of the Invention

The present invention relates to a pump unit for transferring a fluid with a micropump, and a breathing assistance device using the pump unit.

2. Description of the Related Art

A breathing assistance device such as a respirator is being used in the field of medical care. The breathing assistance device employs systems including a controlled ventilation system used for a patient who cannot breathe spontaneously (a patient under general anesthesia or cardiopulmonary resuscitation, or a patient in a critical condition), an assisted ventilation system for generating a positive pressure in a respiratory passage in response to the spontaneous breathing of a patient, an assist-control ventilation system using the assisted ventilation and the controlled ventilation in combination, and a high-frequency oscillation ventilation for realizing a very small amount of single ventilation of from 1 to 2 ml/kg by causing a gas to be supplied to a respiratory passage to oscillate at a frequency of from 5 to 40 Hz.

This breathing assistance device is also used for a patient suffering from a sleep respiratory disorder. This respiratory disorder is caused by blockage of a respiratory passage as a result of relaxation of the muscle of the respiratory passage and a resultant lowered position of root part of a tongue or a soft palate. Applying positive pressure to a respiratory passage also relieves the symptom of a patient suffering from the respiratory disorder of this type.

A breathing assistance device of any type requires a pump unit to generate a positive pressure in a respiratory passage. A blower for transferring a gas by rotating a fan, a cylinder pump for transferring a gas by making reciprocating motion of a piston or the like is used as a power source for the pump unit.

Meanwhile, the pump unit used in a conventional breathing assistance device is of a relatively large a size. Accordingly, the breathing assistance device is housed in a box-shaped casing, and is placed beside a user when it is used. This makes it difficult to realize the compact size of the breathing assistance device.

A pump unit used in a breathing assistance device makes the following control as shown in FIG. 18, for example. The pump unit increases pressure (generates positive pressure) rapidly at a high flow rate in an initial stage during inspiratory operation, and thereafter, maintains a constant flow rate while assisting in the inspiration while further increasing the pressure. Further, during expiratory operation, the pump unit reduces pressure (generates negative pressure) rapidly at a high flow rate, and reduces a flow rate gradually if the pressure turns to decrease to avoid a burden on a lung. This control is only an example, and various control modes are actually required. However, fine control of this type requires a relatively large blower or cylinder pump in order to realize change of pressure and a flow rate freely. This causes a problem in which it is more difficult to reduce the size of the pump unit.

SUMMARY OF THE INVENTION

The present invention has been made in view of the aforementioned problems. It is an object of the invention to provide a pump unit capable of being reduced in size significantly and allowing control of pressure and a flow rate freely, and a breathing assistance device using the pump unit.

The present inventor has made exceptional studies to contrive the following means that achieves the aforementioned object.

More specifically, the present means to achieve the aforementioned object is a pump unit including: a plurality of micropumps arranged in a lattice pattern with rows and columns, the micropumps transferring a fluid in a direction along the columns; an integrated discharge port to which a discharge port of at least a micropump arranged in the most downstream row is directly connected, the integrated discharge port receiving the fluid transferred by the micropumps to be discharged finally through the integrated discharge port; a discharge direct-connection mechanism for connecting respective discharge ports of the plurality of micropumps in a middle row directly to the integrated discharge port; an intake direct-connection mechanism for connecting respective intake ports of the plurality of micropumps in the middle row directly to the fluid to be supplied first; a series-connection mechanism for connecting a discharge port of a micropump in an upstream row directly to an intake port of a micropump in a downstream row; and a controller for controlling the discharge direct-connection mechanism, the intake direct-connection mechanism, and the series-connection mechanism. The controller connects the discharge port of the micropump in the upstream row directly to the intake port of the micropump in the downstream row to form connection in the direction of the columns, thereby bringing the plurality of micropumps in a pressure preferred transfer state. The controller connects the discharge ports of the micropumps in a plurality of rows directly to the integrated discharge port, and connects intake ports of the micropumps in the plurality of rows directly to the fluid to be supplied first, thereby bringing the plurality of micropumps in a flow rate preferred transfer state.

In the above invention, in the pump unit to achieve the aforementioned objet, it is preferable that the number of the micropumps in operation in the downstream row be the same as or smaller than the number of the micropumps in the upstream row in the pressure preferred transfer state.

In the above invention, in the pump unit to achieve the aforementioned objet, it is preferable that the number of the micropumps arranged in the downstream row be the same as or smaller than the number of the micropumps arranged in the upstream row.

In the above invention, it is preferable that the controller of the pump unit to achieve the aforementioned object cause the flow rate preferred transfer state and the pressure preferred transfer state to exist together, and change a relationship between the share of rows to be connected to each other in the pressure preferred transfer state and the share of rows to be directly connected to the integrated discharge port in the flow rate preferred transfer state, thereby changing the pressure and the flow rate of the fluid being transferred stepwise.

In the above invention, it is preferable that the discharge direct-connection mechanism, the intake direct-connection mechanism, and the series-connection mechanism of the pump unit to achieve the aforementioned object switch the connections of all of the plurality of micropumps arranged in the rows at a time.

The present means to achieve the aforementioned object is a pump unit including parallel pump units arranged in a plurality of stages and in each of which a plurality of micropumps are arranged in parallel. The pump unit is provided with: a discharge-side confluence space where flows of a fluid discharged from a plurality of micropumps of an upstream parallel pump unit merge together; an intake-side branching space where flows branching off a fluid are supplied to a plurality of micropumps of a downstream parallel pump unit; a series-connection valve for connecting the discharge-side confluence space for the upstream parallel pump unit directly to the intake-side branching space for the downstream parallel pump unit, or breaking the connection therebetween; a discharge direct-connection valve for connecting the discharge-side confluence space for the upstream parallel pump unit directly to an integrated discharge port through which a fluid is discharged finally, or breaking the connection therebetween; and an intake direct-connection valve for connecting the intake-side branching space for the downstream parallel pump unit directly to the fluid to be supplied first, or breaking the connection therebetween. The discharge-side confluence space, the intake-side branching space, the series-connection valve, the discharge direct-connection valve, and the intake direct-connection valve are provided between the upstream parallel pump unit and the downstream parallel pump unit.

In the above invention, the pump unit to achieve the aforementioned object further includes a controller for controlling the discharge direct-connection valve, the intake direct-connection valve, and the series-connection valve. It is preferable that the controller make switching between a pressure preferred transfer state where the upstream parallel pump unit and the downstream parallel pump unit are connected in series by placing the series-connection valve in a state of forming direct connection and placing the discharge direct-connection valve and the intake direct-connection valve in a shutoff state, and a flow rate preferred transfer state where the upstream parallel pump unit and the downstream parallel pump unit are connected in parallel by placing the series-connection valve in a shutoff state and placing the discharge direct-connection valve and the intake direct-connection valve in a state of forming direct connection.

The present means to achieve the aforementioned object is a breathing assistance device, including: a flow path through which an inspiratory gas or an expiratory gas passes; a nozzle placed in the flow path and through which a gas for acceleration is blown in an expiratory or inspiratory direction; and the pump unit as recited in any one of the aforementioned inventions, the pump unit supplying the gas for acceleration to the nozzle.

The present invention achieves an excellent effect in that the pump unit can be reduced in size significantly while the performance of the pump unit is maintained.

DETAILED DESCRIPTION OF THE PREFERRED EMBODIMENTS

Embodiments of the present invention will now be described below in detail with reference to the drawings.

Figure 1:
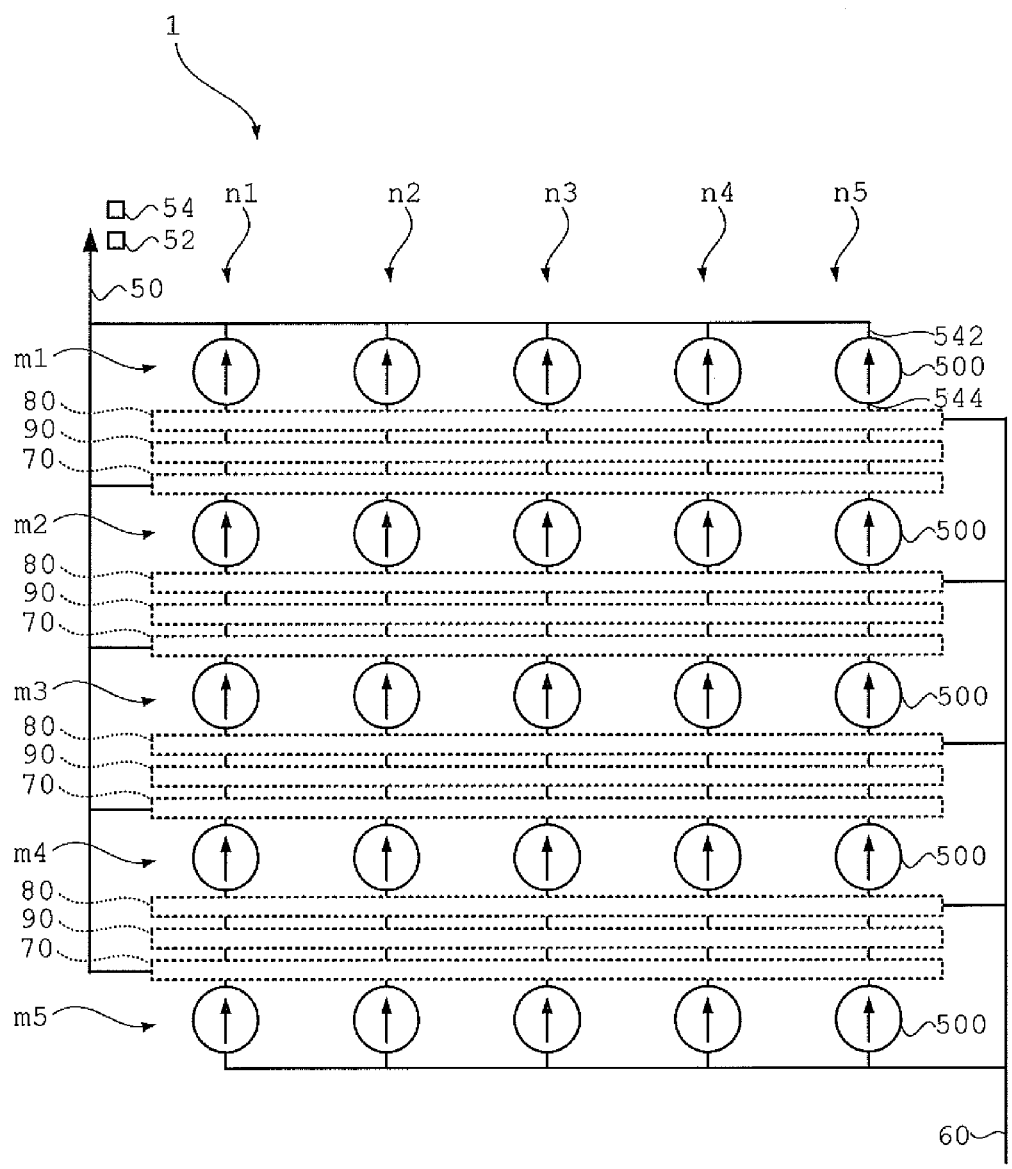
FIG. 1 is a view showing the conceptual structure of a pump unit according to a first embodiment of the present invention.

FIG. 1 shows an example of the conceptual structure of a pump unit 1 according to a first embodiment of the present invention. The pump unit 1 includes a plurality of (here, 25) micropumps 500 arranged in a lattice pattern when viewed conceptually with m1-th to m5-th rows and n1-th to n5-th columns. The micropumps 500 transfer a fluid in a direction along the n1-th to n5-th columns.

Figure 2:
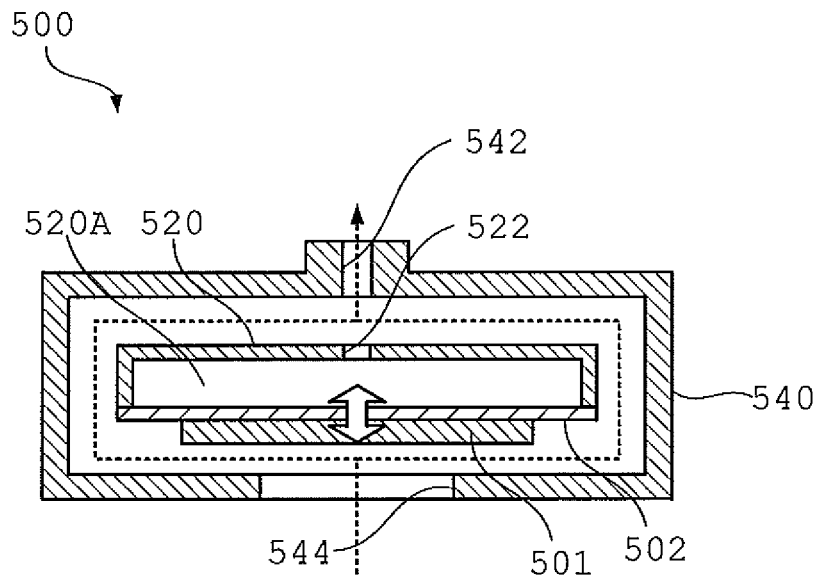
FIG. 2A is a cross-sectional view showing an exemplary structure of a micropump used in the pump unit, and FIG. 2B includes a graph with lines showing the relationship between the pressure and the flow rate of the micropump.
Figure 2:
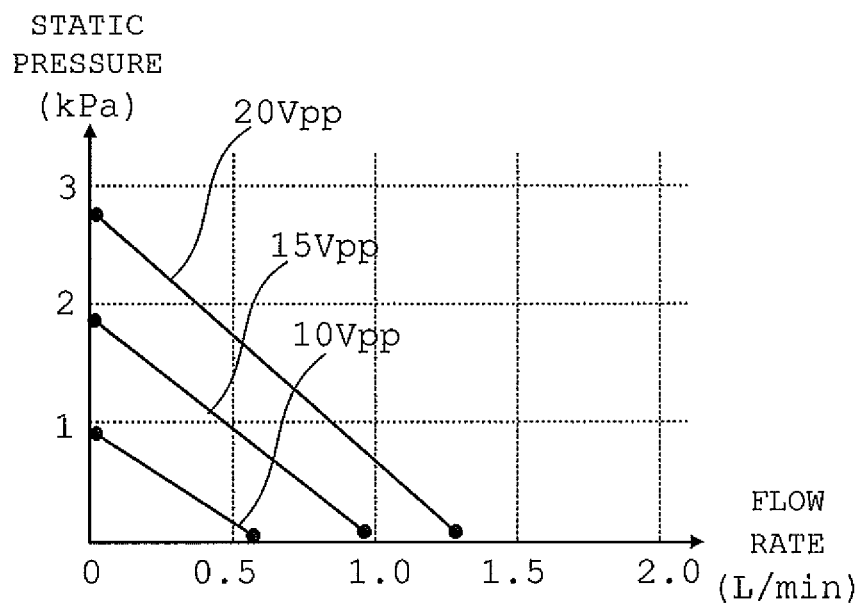

An example of the structure of the micropump 500 is described first by referring to FIG. 2A. The micropump 500 is suggested in patent literature WO 2008/069266. In the micropump 500, a piezoelectric element 501 is fixed to a diaphragm 502, and a vibrating wall 520 is arranged to face the diaphragm 502, thereby forming a first blower chamber 520A. The vibrating wall 520 is provided with an opening 522 through which a fluid moves into and out of the first blower chamber 520A. Further, a second blower chamber 540 communicating with the opening 522 is formed outside the first blower chamber 520A. The second blower chamber 540 is provided with a discharge port 542 at a position facing the opening 522, and an intake port 544 communicating with the circumference of the second blower chamber 540. If the diaphragm 502 is caused to vibrate by the piezoelectric element 501, a fluid moves between the second and first blower chambers 540 and 520A. This generates fluid resistance to cause the vibrating wall 520 to vibrate sympathetically. The sympathetic vibration of the diaphragm 502 and the vibrating wall 520 pumps up the fluid through the intake port 544, and discharges the fluid through the discharge port 542. The micropump 500 is applied suitably for a blower for transferring a gas, and can transfer a gas without requiring a check valve. The micropump 500 is in the shape of a box having a considerably small outer diameter of about 20 mm×20 mm×2 mm. Meanwhile, if an input sine wave is set at 26 kHz under 15 Vpp (volt peak to peak), the micropump 500 can transfer air of up to about 1 L/min (under static pressure of 0 Pa), and can static pressure of up to 2 kPa (under a flow rate of 0 L/min). Meanwhile, the micropump 500 by nature places limitations on the volume of a fluid the micropump 500 can transfer as the micropump 500 transfers a fluid by using the vibration of the diaphragm 502 caused by the piezoelectric element 501. The static pressure versus flow rate characteristics of the micropump 500 are represented by straight lines shown in FIG. 2B. As an example, a flow rate to obtain static pressure of about 1 kPa is 0.5 L/min. Further, changing the Vpp of an input sine wave to 10 or 20 varies the amplitude of the piezoelectric element 501, thereby making it possible to change pressure and a flow rate. Specifically, a flow rate and pressure can be changed smoothly by changing the Vpp of an input sine wave smoothly. Alternatively, a flow rate and pressure can be changed by changing the frequency of an input sine wave. Thus, a flow rate and pressure can be changed smoothly by changing the frequency of an input sine wave smoothly. However, a flow rate and pressure are limited by the performance of a piezoelectric element, and the strength and durability of a material. Generally, the micropump 500 is used at a rated Vpp and a rated frequency.

The micropump 500 introduced here has a monomorph (unimorph) structure where one piezoelectric element is fixed to a diaphragm. The micropump 500 can certainly have a bimorph structure where two piezoelectric elements are fixed together to increase the amount of vibration. The micropump 500 may be of various other structures such as a structure suitable for transfer of a liquid. Accordingly, in the present invention, the micropump 500 can have a structure optimally selected according to the purpose of the micropump 500. Accordingly, while the micropump 500 of the present embodiment can transfer a gas without requiring a check valve, the micropump 500 may be replaced by a micropump with a check valve provided at a discharge or intake port.

Referring back to FIG. 1, the pump unit 1 includes an integrated discharge port 50 and an integrated intake port 60. The integrated discharge port 50 is a member through which a fluid transferred by all the micropumps 500 is discharged finally. Micropumps 500 belonging to at least the most downstream m1-th row are directly connected to the integrated discharge port 50. A flow rate sensor 52 for measuring the flow rate of a fluid discharged through the integrated discharge port 50 and a pressure sensor 54 for detecting the pressure of the fluid are provided near the integrated discharge port 50. The integrated intake port 60 is a member to which a fluid to be transferred by all the micropumps 500 is supplied first. Micropumps 500 belonging to at least the most upstream m5-th row are directly connected to the integrated intake port 60.

The pump unit 1 includes a discharge direct-connection mechanism 70, an intake direct-connection mechanism 80, and a series-connection mechanism 90. The discharge direct-connection mechanism 70 connects the respective discharge ports 542 of micropumps 500 belonging to at least the middle m2-th to m4-th rows directly to the integrated discharge port 50. In particular, in the present embodiment, the respective discharge ports 542 of the micropumps 500 belonging to the most upstream m5-th row can also be directly connected to the integrated discharge port 50. The intake direct-connection mechanism 80 connects the respective intake ports 544 of the micropumps 500 belonging to at least the middle m2-th to m4-th rows directly to the integrated intake port 60. In particular, in the present embodiment, the respective intake ports 544 of the micropumps 500 belonging to the most downstream m1-th row can also be directly connected to the integrated intake port 60.

The series-connection mechanism 90 is provided between micropumps 500 as a pair adjacent to each other in the direction along the columns (vertical direction of the figure). The series-connection mechanism 90 connects the discharge port 542 of a micropump 500 in an upstream row directly to the intake port 544 of a micropump 500 in a downstream row.

In the pump unit 1 of the present embodiment, the discharge direct-connection mechanism 70, the intake direct-connection mechanism 80, and the series-connection mechanism 90 provided for each row switch the connections of all of a plurality of micropumps 500 at a time arranged in each row. Specifically, one discharge direct-connection mechanism 70, one intake direct-connection mechanism 80, and one series-connection mechanism 90 are provided between the m1-th and m2-th rows, between the m2-th and m3-th rows, between the m3-th and m4-th row, and between the m4-th and m5-th rows. The discharge direct-connection mechanism 70 provided between any two of the rows connects the respective discharge ports 542 of micropumps 500 together belonging to a corresponding row directly to the integrated discharge port 50. The intake direct-connection mechanism 80 provided between any two of the rows connects the respective intake ports 544 of the micropumps 500 together belonging to a corresponding row directly to the integrated intake port 60. The series-connection mechanism 90 provided between any two of the rows connects the respective discharge ports 542 of micropumps 500 together belonging to an upstream row directly to the respective intake ports 544 of micropumps 500 belonging to a downstream row. As a result, a valve structure and valve control are simplified. The discharge direct-connection mechanism 70, the intake direct-connection mechanism 80, and the series-connection mechanism 90 may be provided not for each row but for each micropump 500. This results in a complicated structure, but allows control of a higher degree of precision.

Figure 3:
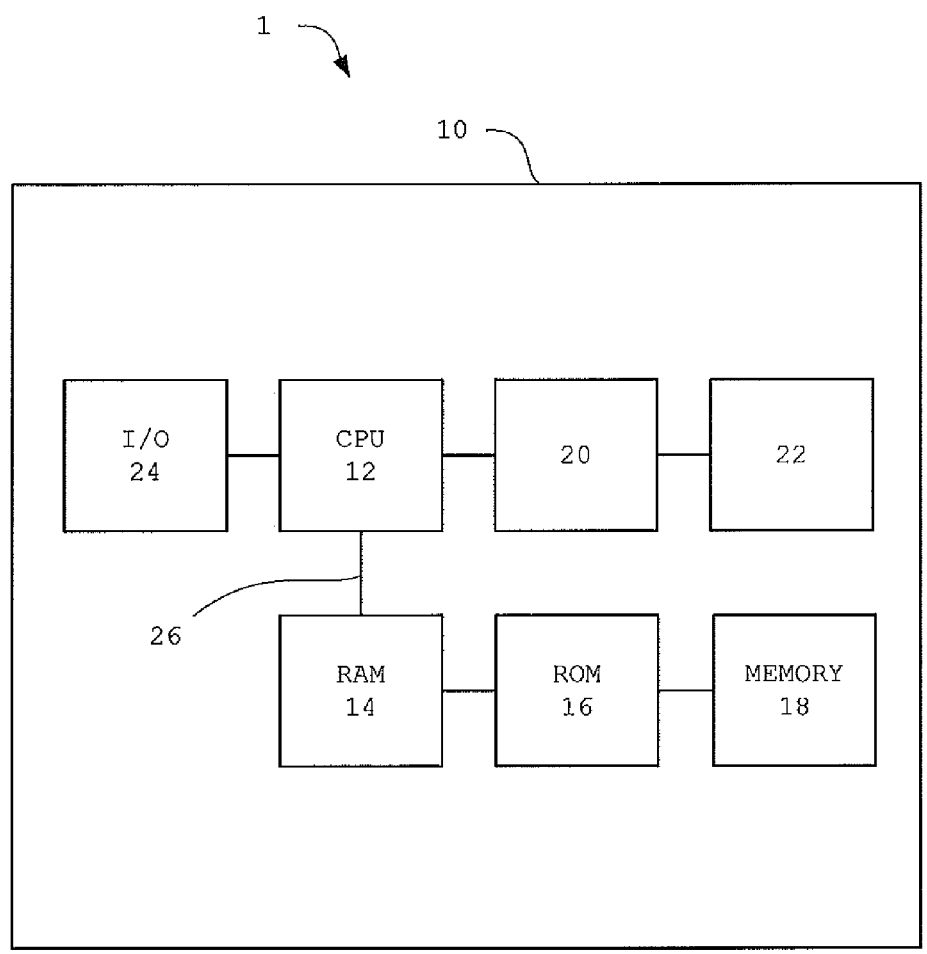
FIG. 3 is a block diagram showing the hardware structure of a controller used in the pump unit.

FIG. 3 shows a controller 10 provided to the pump unit 1. The hardware structure of the controller 10 includes a CPU 12, a first storage medium 14, a second storage medium 16, a third storage medium 18, an input device 20, a display device 22, an input and output interface 24, and a bus 26. The CPU 12 is what is called a central processing unit that executes various programs to realize various functions of the controller 10. The first storage medium 14 is what is called a RAM (random-access memory) used as a working area of the CPU 12. The second storage medium 16 is what is called a ROM (read-only memory) to store a basic OS to be executed by the CPU 12. The third storage medium 18 is composed of a hard disk drive with a built-in magnetic disk, a disk drive to store a CD, a DVD or a BD, a nonvolatile semiconductor flush memory, or the like. The third storage medium 18 stores various programs to be executed by the CPU 12, sensing data obtained from the flow rate sensor 52 and the pressure sensor 54, and others. The input device 20 is composed of input keys, a key board and a mouse, through which information of various types is entered. The display device 22 is a display on which various operating states are displayed. The input and output interface 24 receives and outputs power supplies and control signals for operating the discharge direct-connection mechanism 70, the intake direct-connection mechanism 80 and the series-connection mechanism 90, sensing signals obtained from the flow rate sensor 52 and the pressure sensor 54, and a power supply (having the waveform of a sine wave) and a control signal for operating each of the micropumps 500. The input and output interface 24 can also acquire data such as a program from an external personal computer, and can output a measuring result to the personal computer. The bus 26 is an interconnect line for connecting the CPU 12, the first, second and third storage media 14, 16 and 18, the input device 20, the display device 22, the input and output interface 24 and others integrally to make communications.

Figure 4:
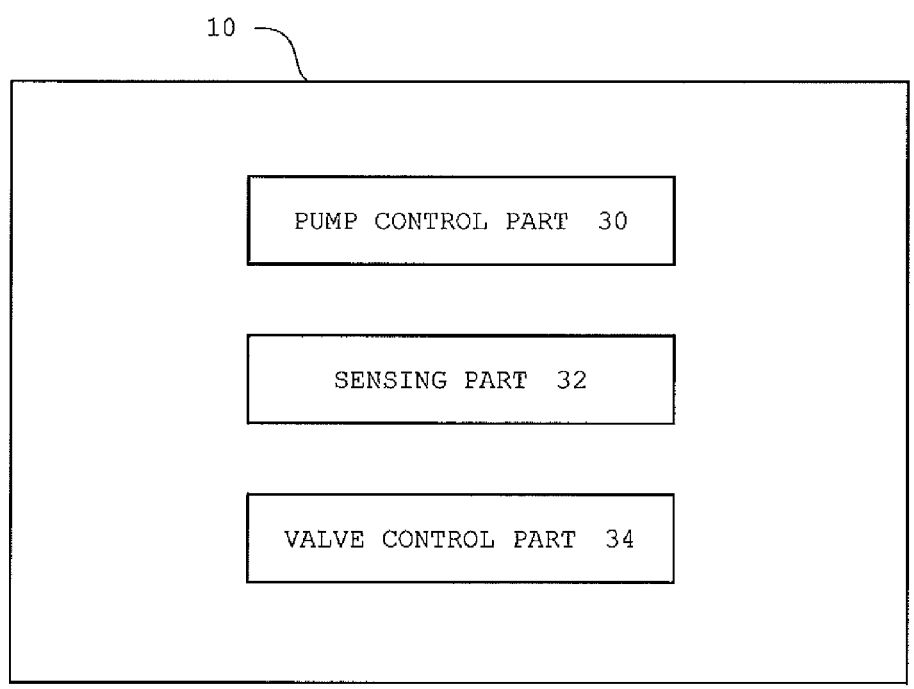
FIG. 4 is a block diagram showing the functional structure of the controller used in the pump unit.

FIG. 4 shows a functional structure realized by execution of a control program stored in the controller 10 by the CPU 12. The functional structure of the controller 10 includes a pump control part 30, a sensing part 32, and a valve control part 34. The pump control part 30 controls the Vpp and the frequency of an input sine wave of the micropumps 500. The sensing part 32 acquires sensing signals all the time obtained from the flow rate sensor 52 and the pressure sensor 54, and transmits the sensing signals to the pump control part 30 and the valve control part 34. The valve control part 34 refers to the sensing signals acquired by the sensing part 32 to switch the discharge direct-connection mechanism 70, the intake direct-connection mechanism 80, and the series-connection mechanism 90 suitably, thereby controlling a flow rate and pressure such that they get closer to their target values.

Figure 5:
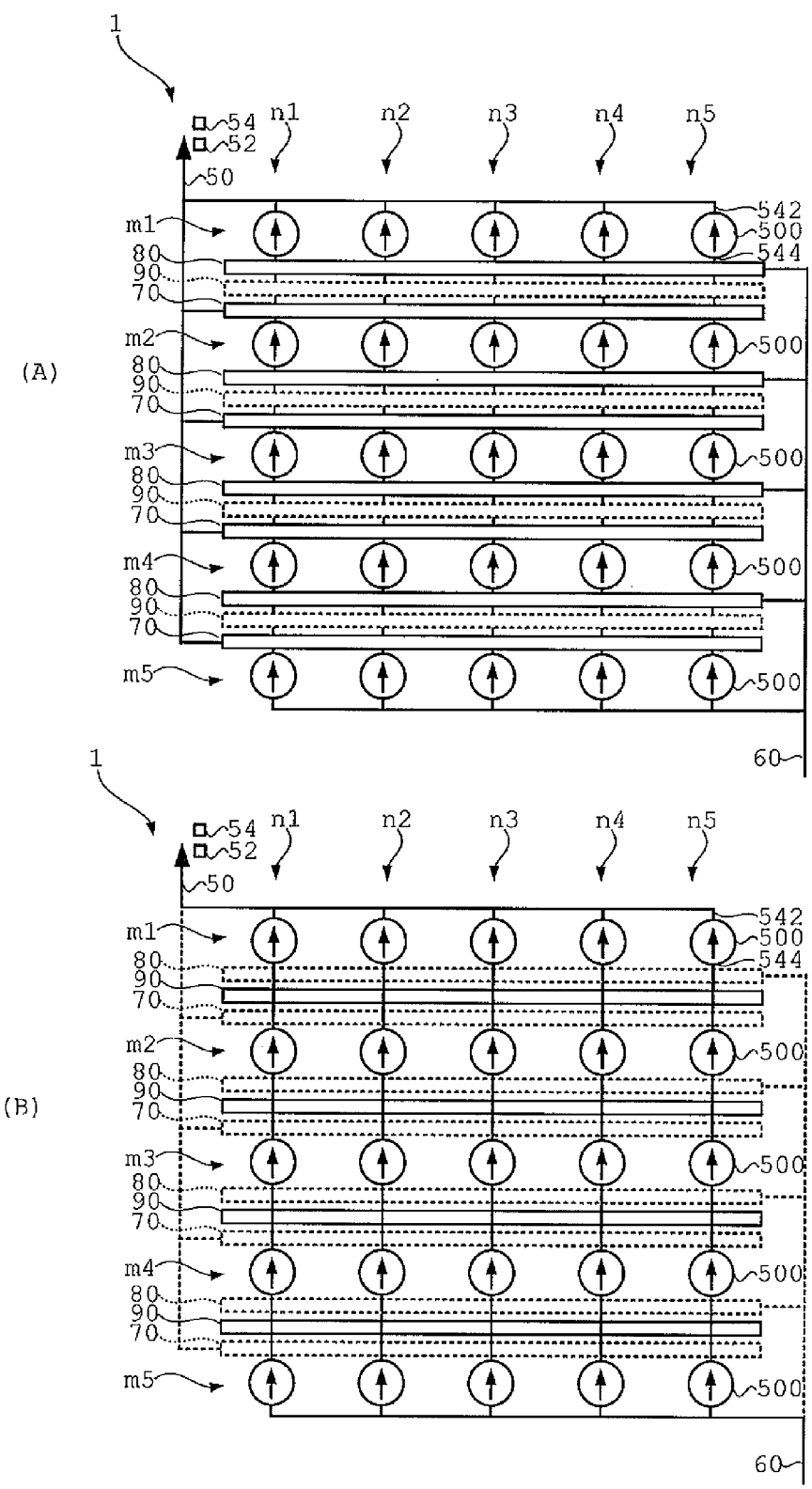
FIGS. 5A and 5B are views showing examples of control of the pump unit.

An example of control of the pump unit 1 by the controller 10 is shown in FIG. 5.

In the pump unit 1 shown in FIG. 5A, all the discharge direct-connection mechanisms 70 and all the intake direct-connection mechanisms 80 are turned on and all the series-connection mechanisms 90 are turned off. Accordingly, the discharge ports 542 of the micropumps 500 in the m1-th to m5-th rows are directly connected to the integrated discharge port 50, and the intake ports 544 of the micropumps 500 in the m1-th to m5-th rows are directly connected to the integrated intake port 60. As a result, the 25 micropumps 500 are connected in parallel to bring all the rows into a transfer state where precedence is given to a flow rate (here, this is called a flow rate preferred transfer state). This can achieve a flow rate 25 times higher than that achieved by a single micropump 500.

In the pump unit 1 shown in FIG. 5B, all the discharge direct-connection mechanisms 70 and all the intake direct-connection mechanisms 80 are turned off, and all the series-connection mechanisms 90 are turned on. Accordingly, the discharge ports 542 of micropumps 500 in upstream rows are directly connected to the intake ports 544 of micropumps 500 in downstream rows. As a result, micropumps 500 in five stages are connected in series in the direction along the n1-th to n5-th columns to bring all the rows into a transfer state where precedence is given to pressure (here, this is called a pressure preferred transfer state). Thus, pressure of a fluid increases as the fluid goes further downstream, so that pressure of about five times higher can be obtained at the outlet. Further, five micropumps 500 are connected in parallel in each of the m1-th to m5-th rows. Thus, the resultant flow rate can be about five times the flow rate obtained in the case where five micropumps 500 are simply connected in series.

Figure 6:
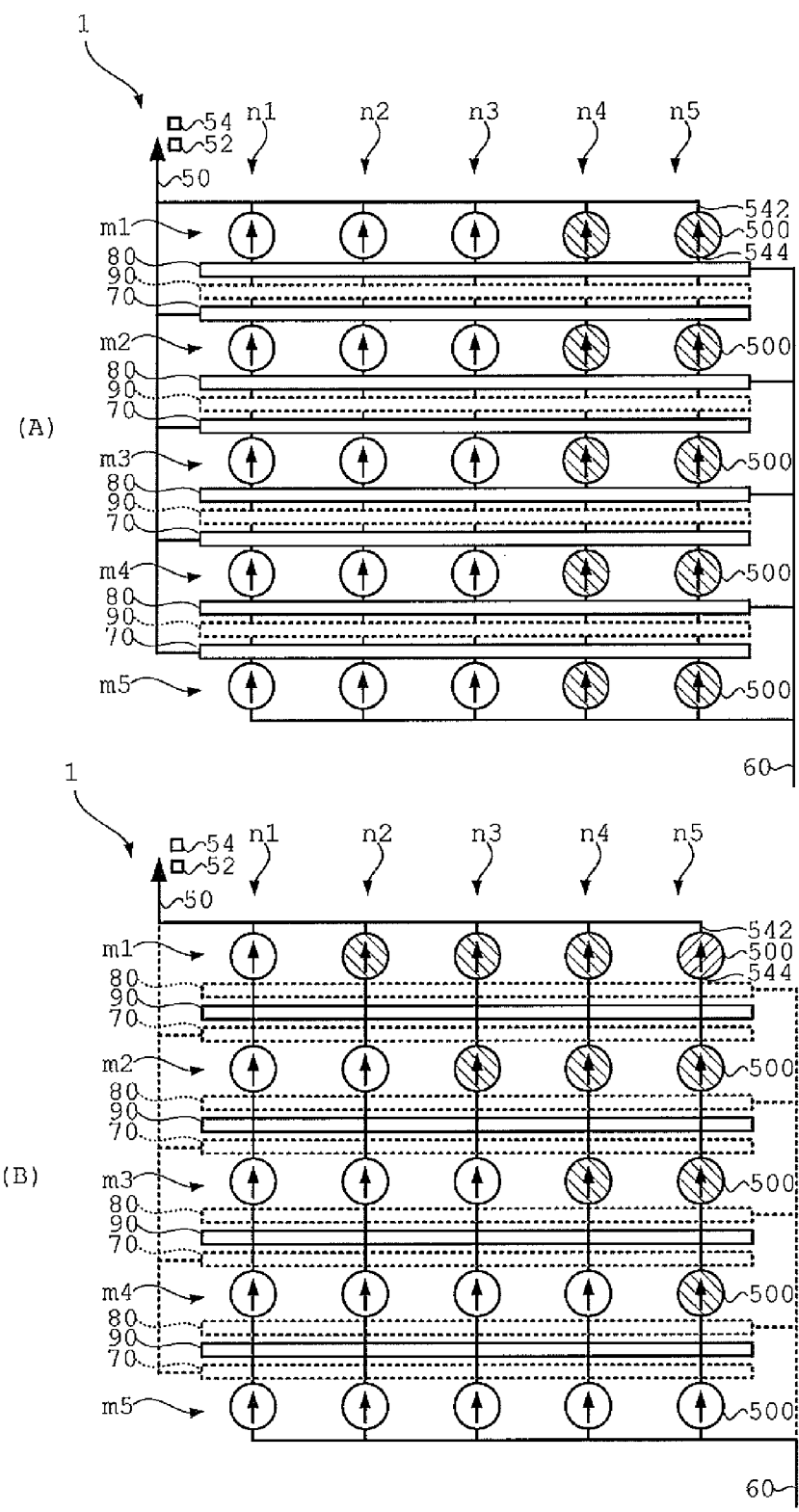
FIGS. 6A and 6B are views showing examples of control of the pump unit.

All the micropumps 500 are in operation in the example of the flow rate preferred transfer state shown in FIG. 5A. However, it is preferable that a flow rate be controlled while the number of micropumps 500 in operation is reduced in each row as shown in the example of FIG. 6A. In FIG. 6A, micropumps 500 in a halt state are given diagonal lines. Assuming that the flow rate of a single micropump 500 is 1, the resultant flow rate can be changed in the range of from 1 to 25.

All the micropumps 500 are in operation in the example of the pressure preferred transfer state shown in FIG. 5B. However, it is preferable that control be made such that the number of micropumps 500 in operation in a downstream row is the same as or smaller than the number of micropumps 500 in operation in an upstream row. The reason therefor is as follows. In the case of transfer of gas, for example, the volume of the gas degreases as the pressure of the gas increases in a direction from the m5-th row toward the m1-th row in accordance with the Boyle's law. Accordingly, a sufficient flow rate can be maintained without the need of driving all the micropumps 500 in each row. As shown for example in FIG. 6B, five micropumps 500 are in operation in the m5-th row, four micropumps 500 are in operation in the m4-th row, three micropumps 500 are in operation in the m3-th row, two micropumps 500 are in operation in the m2-th row, and one micropump 500 is in operation in the m1-th row. If static pressure is increased at a rate of 1 kPa from row to row, static pressure of 5 kPa is obtained at the integrated discharge port 50, and the volume (flow rate) of the gas is reduced to about one fifth. As a result, a flow rate in the m1-th row does not exceed the maximum allowable flow rate of one micropump 500. Thus, a flow rate obtained in the m1-th row by operating one micropump 500 can be the same as the corresponding flow rate obtained in FIG. 5B. That is, as the same output can be obtained from FIGS. 5B and 6B, FIG. 6B is preferable in terms of energy efficiency. In the example of FIG. 6B, the number of micropumps 500 in operation is always lower in a downstream row than in an upstream row, to which the invention is not limited. If the number of micropumps 500 in operation is lower at least in a downstream row than in a corresponding upstream row, it is not necessarily reduced from row to row.

Figure 7:
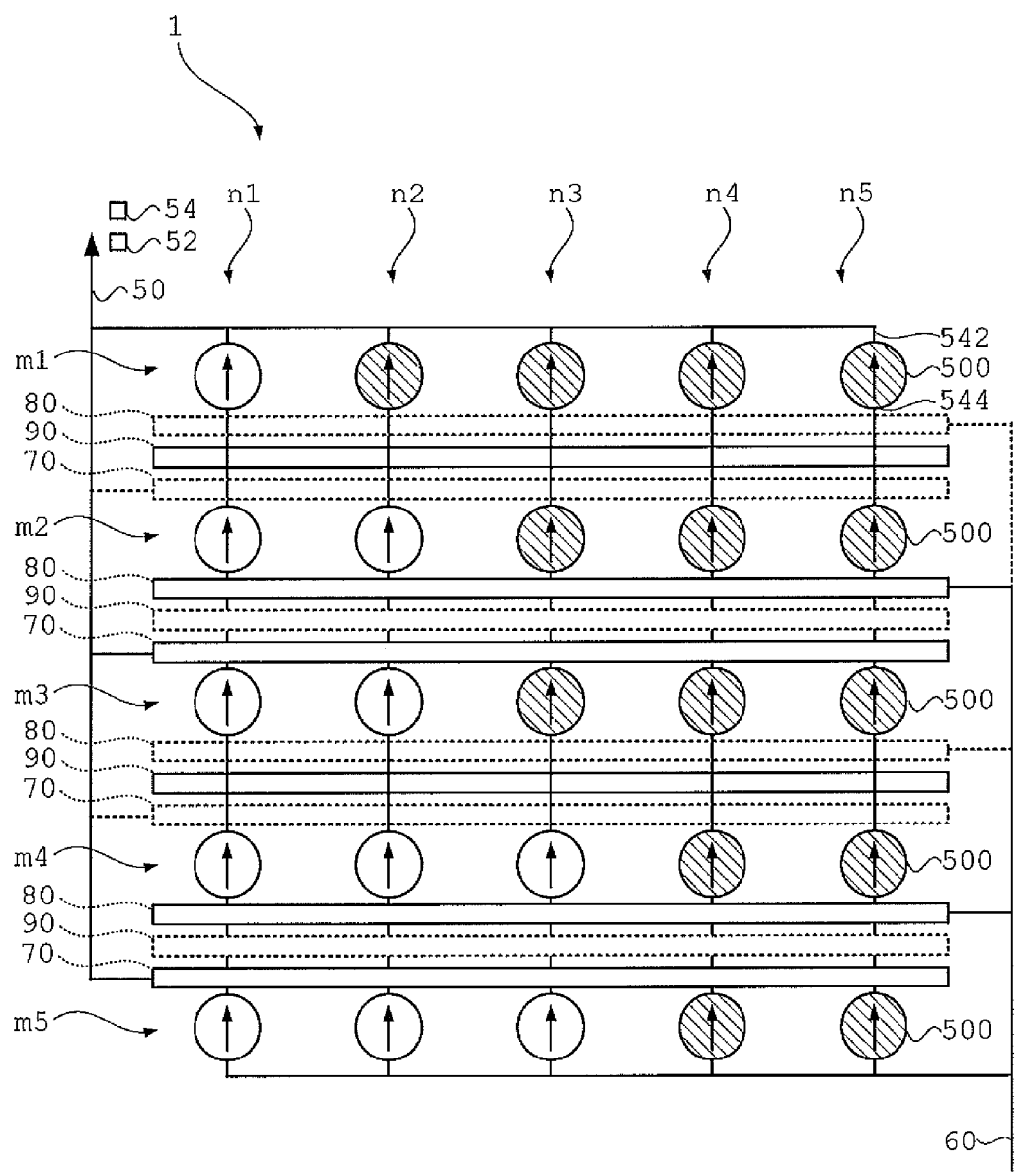
FIG. 7 is a view showing examples of control of the pump unit.

It is also preferable that the flow rate preferred transfer state and the pressure preferred transfer state exist together as shown in FIG. 7. In FIG. 7, the pressure preferred transfer state is formed between the m1-th and m2-th rows, the flow rate preferred transfer state is formed between the m2-th and m3-th rows, the pressure preferred transfer state is formed between the m3-th and m4-th rows, and the flow rate preferred transfer state is formed between the m4-th and m5-th rows. Further, the number of micropumps 500 in operation is suitably controlled in each row. Accordingly, a relationship between the share of rows as a pair connected to each other in the pressure preferred transfer state, and the share of rows directly connected to the integrated discharge port 50 in the flow rate preferred transfer state is changed to change the pressure and the flow rate of a fluid being transferred stepwise. This produces a wide variety of combinations including the number of micropumps 500 in operation, so that a flow rate and pressure can be determined optimally.

Figure 8:
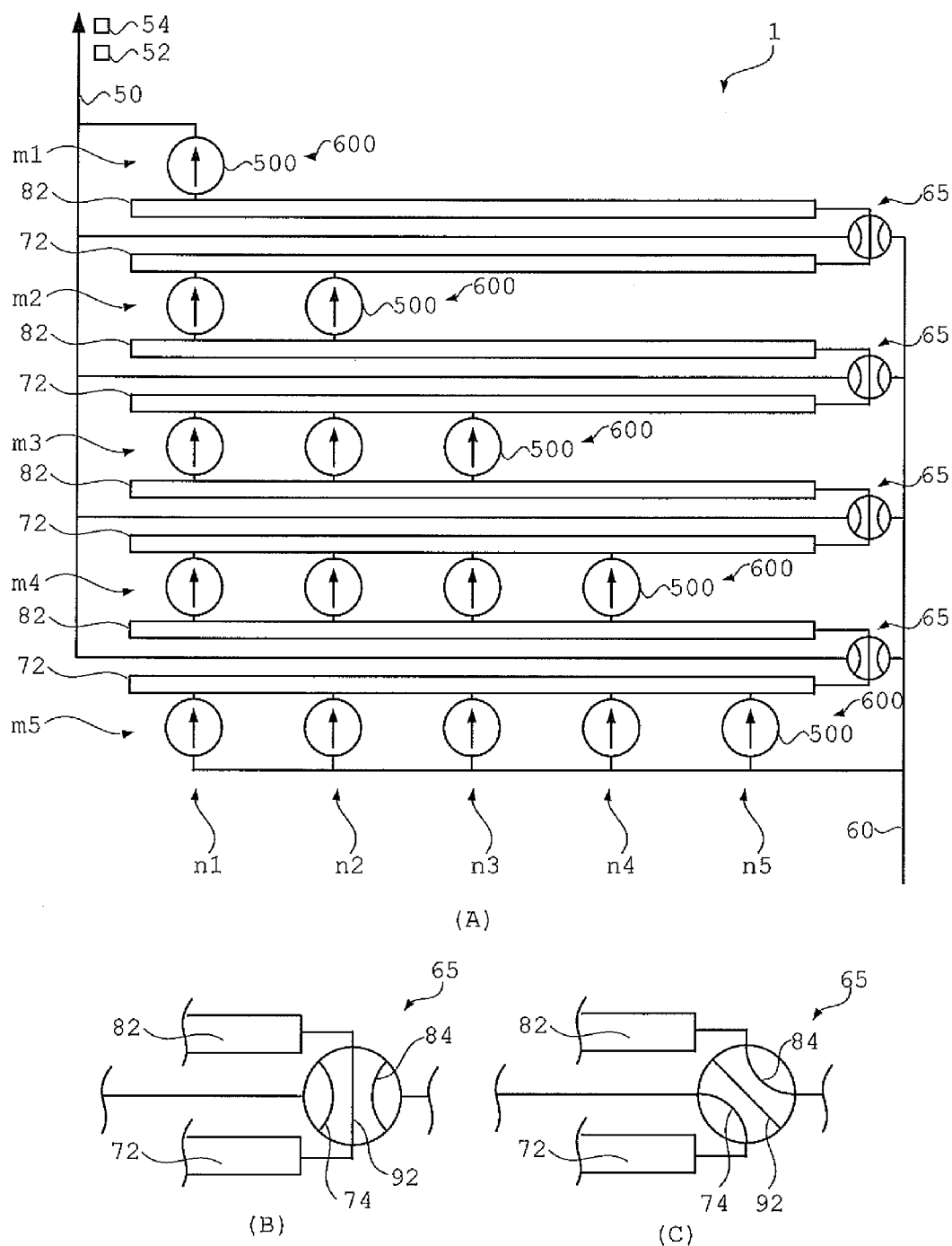
FIGS. 8A, 8B and 8C are views showing the conceptual structure of a pump unit according to a second embodiment of the present invention.

FIG. 8A shows an example of the structure of a pump unit 1 according to a second embodiment. The first and second embodiments include the same or similar parts. Accordingly, these parts will not be described repeatedly, and differences from the first embodiment are mainly described below.

Like the pump unit 1 of the first embodiment, the pump unit 1 of the second embodiment includes micropumps 500 arranged in a lattice pattern when viewed conceptually with m1-th to m5-th rows and n1-th to n5-th columns. Further, the number of micropumps 500 in a downstream row is the same as or smaller than the number of micropumps 500 in an upstream row. More specifically, five micropumps 500 are arranged in parallel in the m5-th row, four micropumps 500 are arranged in parallel in the m4-th row, three micropumps 500 are arranged in parallel in the m3-th row, two micropumps 500 are arranged in parallel in the m2-th row, and one micropump 500 is arranged in the m1-th row. In this example, the number of micropumps 500 in operation is always lower in a downstream row than in an upstream row, to which the invention is not limited.

In the second embodiment, micropumps 500 arranged in parallel in each row are collectively called a parallel pump unit 600. Accordingly, the pump unit 1 of the second embodiment includes parallel pump units 600 in five stages in the m1-th to m5-th rows. The pump unit 1 of the second embodiment further includes a discharge-side confluence space 72, a discharge direct-connection valve 74, an intake-side branching space 82, an intake direct-connection valve 84, and a series-connection valve 92 provided between an upstream parallel pump unit 600 and a downstream parallel pump unit 600 as shown in an enlarged manner in FIGS. 8B and 8C. The discharge direct-connection valve 74, the intake direct-connection valve 84, and the series-connection valve 92 are operated together by rotating one switching valve 65. A rotating type is not the only type of the switching valve 65, but the switching valve 65 may be of a type using an electromagnetic valve and the like.

The discharge-side confluence space 72 is a chamber space where all flows of a fluid discharged from a plurality of micropumps 500 of an upstream parallel pump unit 600 merge together. The discharge direct-connection valve 74 is a valve for connecting the discharge-side confluence space 72 directly to the integrated discharge port 50 through which a fluid is discharged finally, or breaking the connection therebetween as shown in FIG. 8C.

The intake-side branching space 82 is a space where flows branching off a fluid are supplied to a plurality of micropumps 500 of a downstream parallel pump unit 600. Specifically, the intake-side branching space 82 is a chamber space where the intake ports 544 of these micropumps 500 are connected together. The intake direct-connection valve 84 is a valve for connecting the intake-side branching space 82 directly to the integrated intake port 60 through which a fluid is supplied first, or breaking the connection therebetween as shown in FIG. 8C.

The series-connection valve 92 is a valve for connecting the upstream discharge-side confluence space 72 directly to the downstream intake-side branching space 82, or breaking the connection therebetween as shown in FIG. 8B.

Accordingly, in terms of correspondence to the discharge direct-connection mechanism 70, the intake direct-connection mechanism 80 and the series-connection mechanism 90 of the first embodiment, the discharge-side confluence space 72 and the discharge direct-connection valve 74 correspond to the discharge direct-connection mechanism 70, the intake-side branching space 82 and the intake direct-connection valve 84 correspond to the intake direct-connection mechanism 80, and the discharge-side confluence space 72, the intake-side branching space 82 and the series-connection valve 92 correspond to the series-connection mechanism 90.

In the pump unit 1 of the second embodiment, the discharge-side confluence space 72, the intake-side branching space 82, and the switching valve 65 provided for each parallel pump unit 600 switch the connections of all micropumps 500 belonging to each parallel pump unit 600 at a time.

Figure 9:
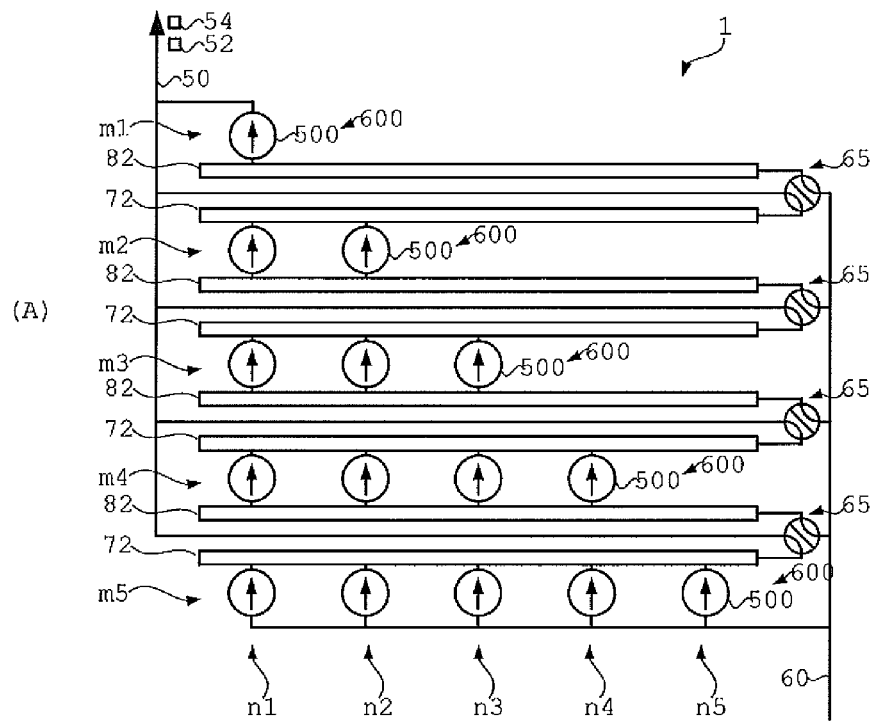
FIGS. 9A and 9B are views showing examples of control of the pump unit.
Figure 9:
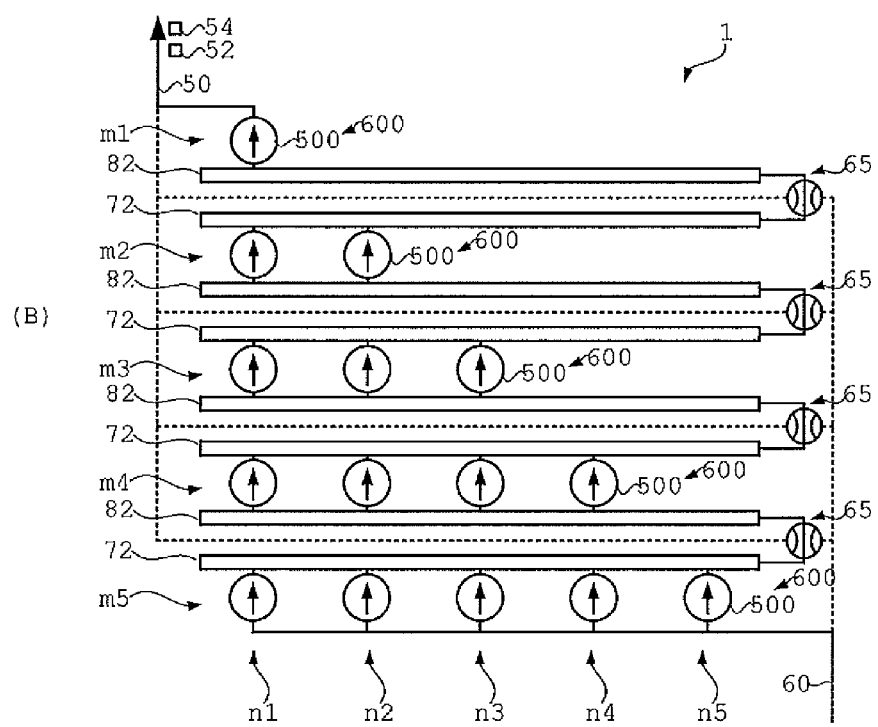

FIGS. 9A and 9B show examples of control of the pump unit 1 of the second embodiment that is also made by the controller 10 of FIG. 1.

In FIG. 9A, all the series-connection valves 92 are in a shutoff state (OFF), and all the discharge direct-connection valves 74 and the intake direct-connection valves 84 are in a state of forming direction connection (ON). Accordingly, all the upstream parallel pump units 600 and downstream parallel pump units 600 are connected in parallel. Accordingly, the discharge ports 542 of all the micropumps 500 are directly connected to the integrated discharge port 50, and the intake ports 544 of all the micropumps 500 are directly connected to the integrated intake port 60. As a result, 15 micropumps 500 are connected in parallel to make the flow rate preferred transfer state. This can achieve a flow rate 15 times higher than that achieved by a single micropump 500.

In FIG. 9B, all the series-connection valves 92 are in a state of forming direction connection, and all the discharge direct-connection valves 74 and the intake direct-connection valves 84 are in a shutoff state. Accordingly, this forms series connections between corresponding upstream parallel pump units 600 and corresponding downstream parallel pump units 600. This makes the pressure preferred transfer state where the parallel pump units 600 in five stages are connected in series. In particular, provision of the discharge-side confluence spaces 72 and the intake-side branching spaces 82 at midpoints in a flow path equalizes the pressure of a fluid to be supplied to and discharged from the respective micropumps 500. Thus, a load to be placed on the micropumps 500 can be equalized, making it possible to enhance transfer efficiency.

Figure 10:
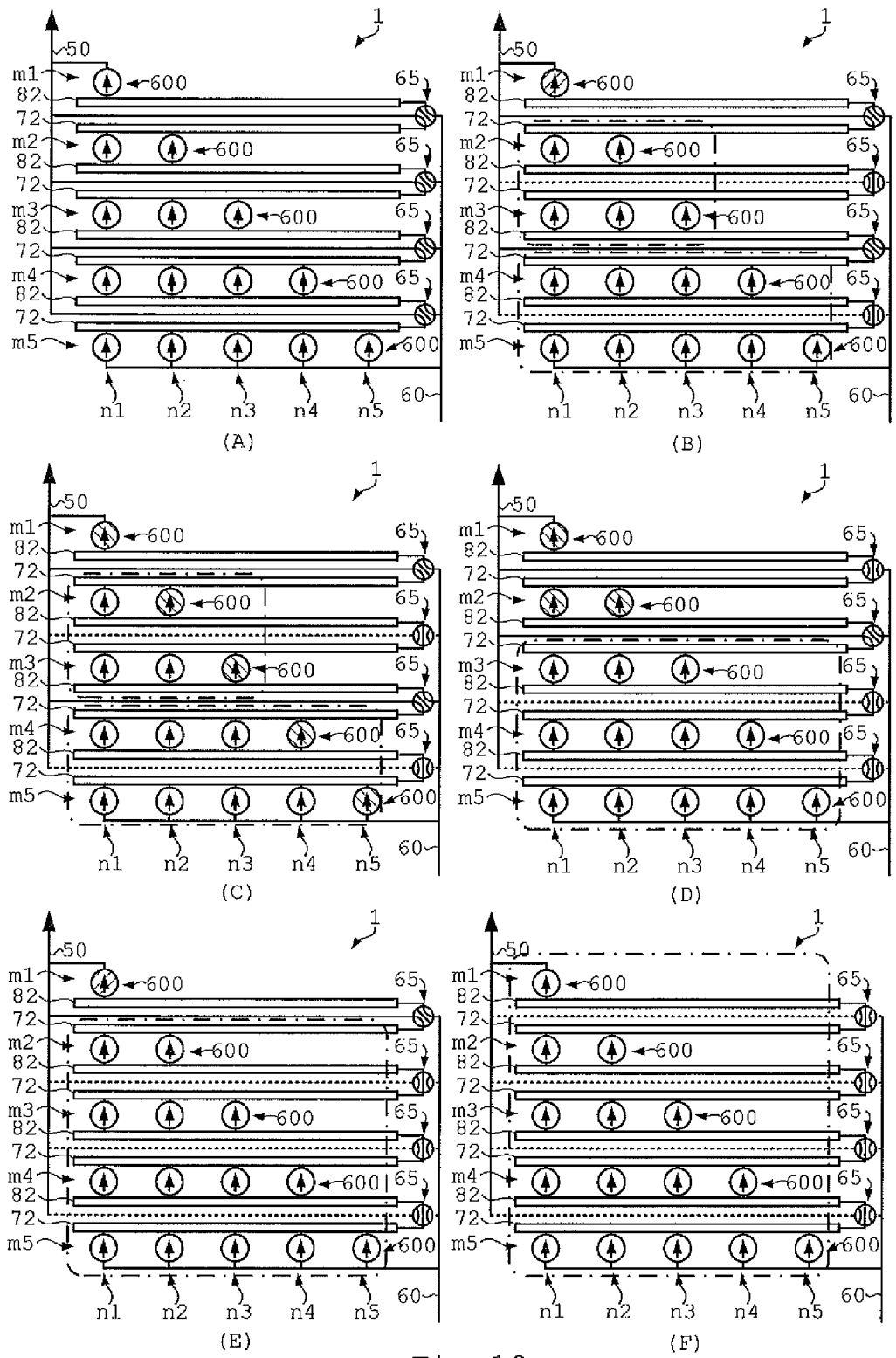
FIGS. 10A to 10F are views showing examples of control of the pump unit.

FIG. 10 shows examples of control realized by using the pump unit 1 of the second embodiment in order to make stepwise switching from a high flow rate state to a high pressure state. First, as shown in FIG. 10A, all the discharge-side confluence spaces 72, all the intake-side branching spaces 82, and all the switching valves 65 are brought into the flow rate preferred transfer state to connect the 15 micropumps 500 in parallel. Accordingly, the resultant pressure is of a magnification of 1 and the resultant flow rate is 15 times higher.

Next, as shown in FIG. 10B, the discharge-side confluence space 72, the intake-side branching space 82, and the switching valve 65 between the parallel pump units 600 in the m2-th and m3-th rows are switched to the pressure preferred transfer state. Further, the discharge-side confluence space 72, the intake-side branching space 82, and the switching valve 65 between the parallel pump units 600 in the m4-th and m5-th rows are switched to the pressure preferred transfer state. As a result, the parallel pump units 600 in these rows realize two-stage series connection, so that the resultant pressure can be twice higher. Further, the resultant flow rate obtained from six micropumps 500 in the m2-th and m4-th rows is six times higher. In this case, the parallel pump unit 600 in the m1-th row is in a halt state.

Further, as shown in FIG. 10C, while the same connections as those of FIG. 10B are formed, one micropump 500 is placed in a halt state in the parallel pump unit 600 in each of m2-th to m5-th rows. Accordingly, the resultant flow rate obtained from parallel-connected four micropumps is four times higher while doubled pressure is maintained. In this case, a flow rate is reduced by bringing micropumps 500 into a halt state. This situation is also formed by switching the discharge-side confluence spaces 72, the intake-side branching spaces 82, and the switching valves 65 between the m1-th and m2-th rows, and between the m3-th and m4-th rows to the pressure preferred transfer state, for example.

Next, as shown in FIG. 10D, the discharge-side confluence spaces 72, the intake-side branching spaces 82, and the switching valves 65 between the m3th and m4th rows, and between the m4th and m5th rows are switched to the pressure preferred transfer state to realize three-stage series connection. Accordingly, the resultant pressure is three times higher and the resultant flow rate obtained from three micropumps 500 of the parallel pump unit 600 in the m3-th row is three times higher. In this case, the parallel pump units 600 in the m1-th and m2-th rows are in a halt state.

Next, as shown in FIG. 10E, the discharge-side confluence spaces 72, the intake-side branching spaces 82, and the switching valves 65 between the m2-th and m3-th rows, between the m3-th and m4-th rows, and between the m4-th and m5-th rows are switched to the pressure preferred transfer state to realize four-stage series connection. Accordingly, the resultant pressure is four times higher and the resultant flow rate obtained from two micropumps 500 of the parallel pump unit 600 in the m2-th row is twice higher. In this case, the parallel pump unit 600 in the m1-th row is in a halt state.

Finally, as shown in FIG. 10F, all the discharge-side confluence spaces 72, the intake-side branching spaces 82, and the switching valves 65 are switched to the pressure preferred transfer state to realize five-stage series connection. Accordingly, the resultant pressure is five times higher and the resultant flow rate obtained from one micropump 500 of the parallel pump unit 600 in the m1-th row is of a magnification of 1. In this case, each micropump 500 of each parallel pump unit 600 is in operation.

Figure 11:
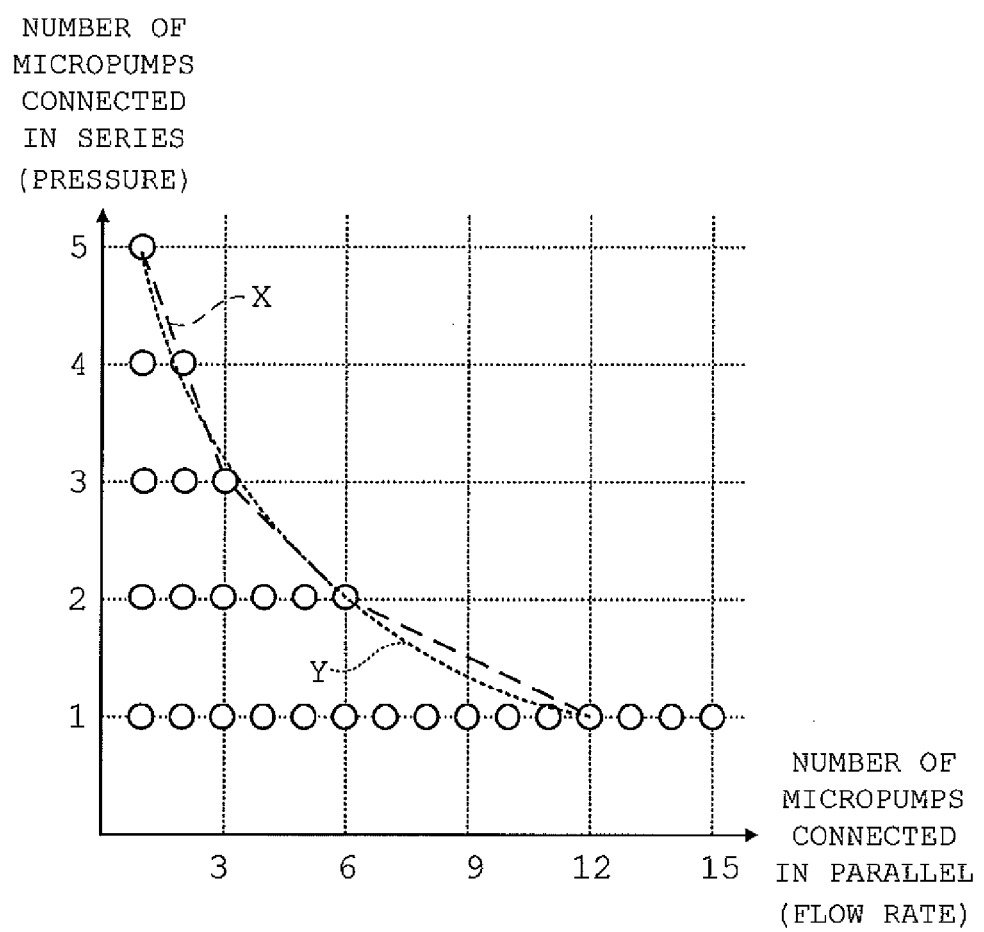
FIG. 11 is a graph showing the number of micropumps connected in series and the number of micropumps connected in parallel that can be selected in the pump unit.

The control described above allows selection of the number of stages of micropumps 500 connected in series and the number of micropumps 500 connected in parallel with variations such as those shown in FIG. 11. Accordingly, a relationship between a flow rate and pressure can be changed smoothly by changing a relationship between the share of micropumps 500 connected in parallel and the share of micropumps 500 connected in series stepwise. As an example, control to make smooth transitions between high pressure transfer and high flow rate transfer shown by dashed line X can be realized. In addition, a relationship between a flow rate and pressure can be changed more smoothly by changing the Vpp or frequency of an input sine wave smoothly. As an example, control to make smooth transitions between high pressure transfer and high flow rate transfer shown by dotted line Y can be realized.

As described above, in the pump unit 1 of the aforementioned embodiments, the micropumps 500 are arranged in a lattice pattern, and the discharge direct-connection mechanisms 70, the intake direct-connection mechanisms 80, and the series-connection mechanisms 90 can make control by combining series connections and parallel connections of the respective micropumps 500 reasonably. A flow rate and static pressure obtained by a single micropump 500 may not be enough to achieve an intended purpose. In contrast, a plurality of micropumps 500 can be used in combination, so that the pump unit 1 can be used in the same manner as a conventional blower or a syringe pump. Further, each micropump 500 has a small size, so that the pump unit 1 in which a plurality of micropumps 500 are arranged can still be smaller and lighter in weight than a conventional blower and the like. Specifically, a wide range of variation of a combination of the number of micropumps 500 connected in parallel and the number of micropumps 500 connected in series can be controlled digitally by turning each micropump 500, the discharge direct-connection mechanism 70, the intake direct-connection mechanism 80, and the series-connection mechanism 90 on or off, making it possible to design a considerably simple control structure. Additionally, failure of even one conventional blower or one conventional syringe pump suspends entire transfer of a fluid. In contrast, in the pump unit 1 of the present embodiments, a different micropump 500 can compensate for the failure of one micropump 500, allowing increase of safety.

In particular, in the pump unit 1 of the present embodiments, the number of micropumps 500 in a downstream row is the same as or smaller than the number of micropumps 500 in an upstream row in the pressure preferred transfer state where the micropumps 500 are connected in series. This suppresses the operation of an unnecessary micropump 500 to allow reduction of power to be consumed. Accordingly, the pump unit 1 is suitably applied especially for the purpose of driving a battery, for example.

Further, the pump unit 1 of the present embodiments switches the connections of all of a plurality of micropumps 500 (entire parallel pump unit 600) arranged in each row at a time. This simplifies a valve structure to enhance the performance of maintenance. In particular, provision of the discharge-side confluence space 72 and the intake-side branching space 82 between the parallel pump units 600 as a pair of the second embodiment simplifies the unit structure. The discharge-side confluence spaces 72 and the intake-side branching spaces 82 provided at midpoints function as buffer spaces. Accordingly, if the number of micropumps 500 of the parallel pump unit 600 is reduced in a direction from the most upstream part toward the most downstream part, for example, complicated pipe structure is not required. Further, the number of micropumps 500 connected in parallel in the unit parallel pump unit 600 can be increased and decreased easily only by turning micropumps 500 belonging to each parallel pump unit 600 on or off without requiring opening and closing control of each valve, so that control can be made easily. In addition, equalizing the pressure of a fluid being transferred in the parallel pump unit 600 leads to enhancement of transfer efficiency.

In the example shown in the present embodiments, a fluid is supplied first to the integrated intake port 60, and then flows branching off the fluid are connected to the intake port 544 of each micropump 500, to which the invention is not limited.

Figure 12:
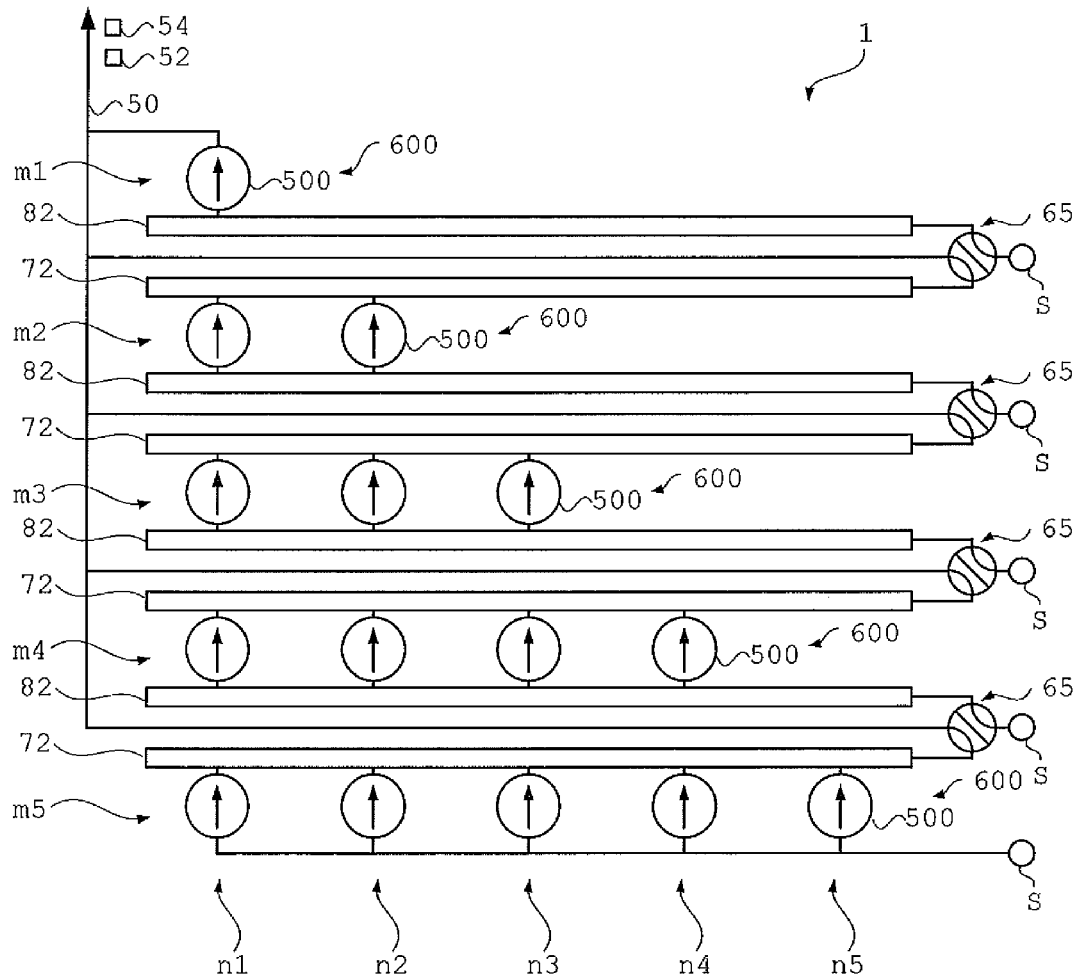
FIG. 12 is a view showing another example of the structure of the pump unit.

If the pump unit 1 is used as a blower to transfer a gas, for example, intake can also be made in a manner shown in FIG. 12 where the respective intake ports 544 of the micropumps 500 or the intake-side branching spaces 82 may individually be exposed to the atmosphere S. This allows intake of gases of two types or more separately. As an example, a first fluid (such as oxygen) is drawn through the intake-side branching spaces 82 between the m1-th and m2-th rows and between the m2-th and m3-th rows. At the same time, a second fluid (such as air) can be drawn through the intake-side branching spaces 82 between the m3-th and m4-th rows and between the m4-th and m5-th rows, and through the respective intake ports 544 of the micropumps 500 in the m5-th row.

Figure 13:
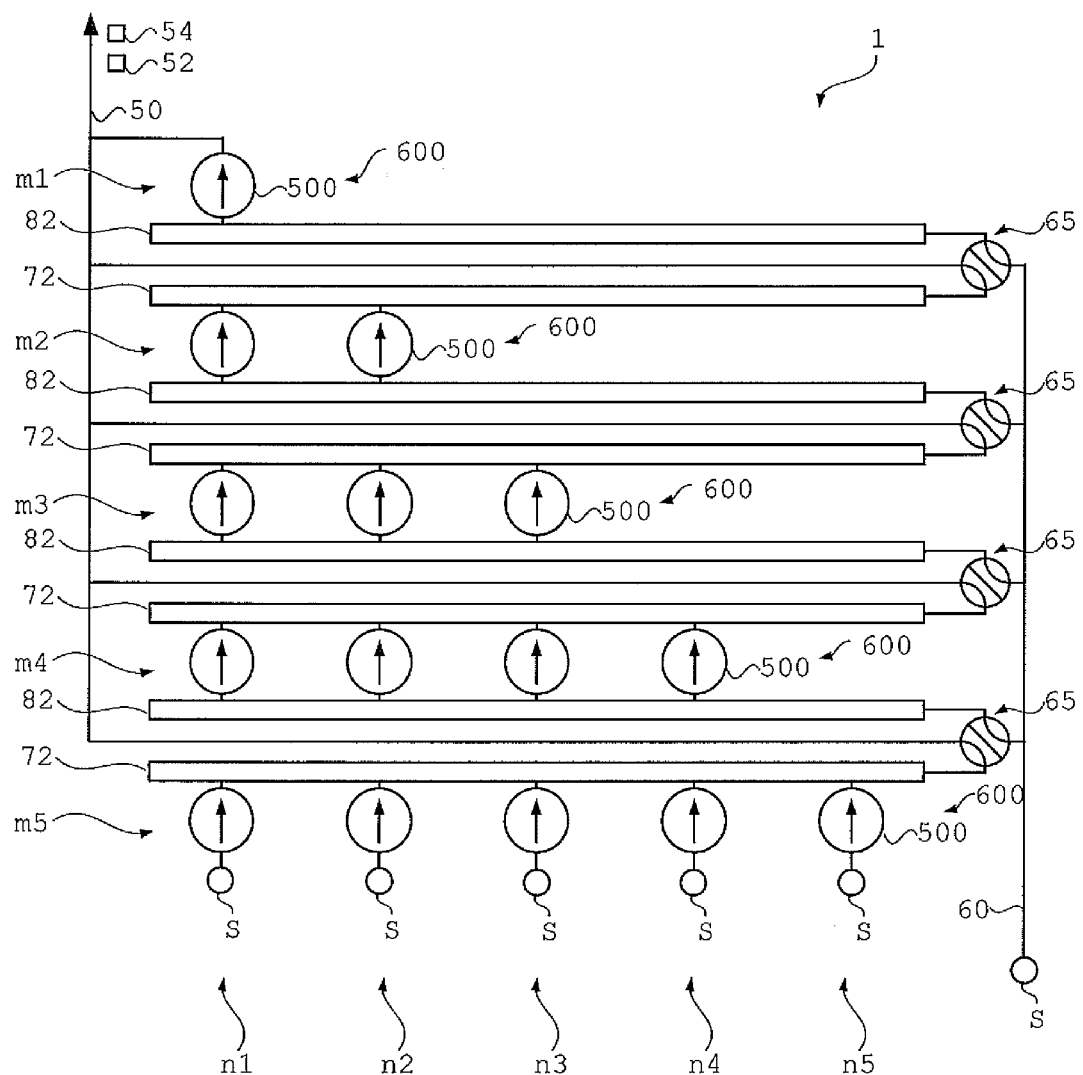
FIG. 13 is a view showing still another example of the structure of the pump unit.

Intake can also be made in a manner shown in FIG. 13 where the respective intake ports 544 of the micropumps 500 in the most upstream m5-th row are individually exposed to the atmosphere S besides the integrated intake port 60. This allows intake of gases of two types or more separately. As an example, a first fluid (such as oxygen) is drawn through the integrated intake port 60, and through the intake ports 544 of the micropumps 500 in the m5-th row and in the n1-th to n3-th columns. At the same time, a second fluid (such as air) can be drawn through the intake ports 544 of the micropumps 500 in the m5-th row and in the n4-th and n5-th columns. In these examples, the first and second fluids are mixed, and then discharged through the integrated discharge port 50.

The lattice arrangement of the micropumps 500 forms the appearance of the pump unit 1 of the present embodiments. However, this appearance is given for the convenience of description. What is required is to form a path for a fluid in the same state as that of the present embodiments. Specifically, what is required is to form the structure of a path for a fluid into a lattice pattern, and layout or structure of hardware can certainly be changed freely.

Figure 14:
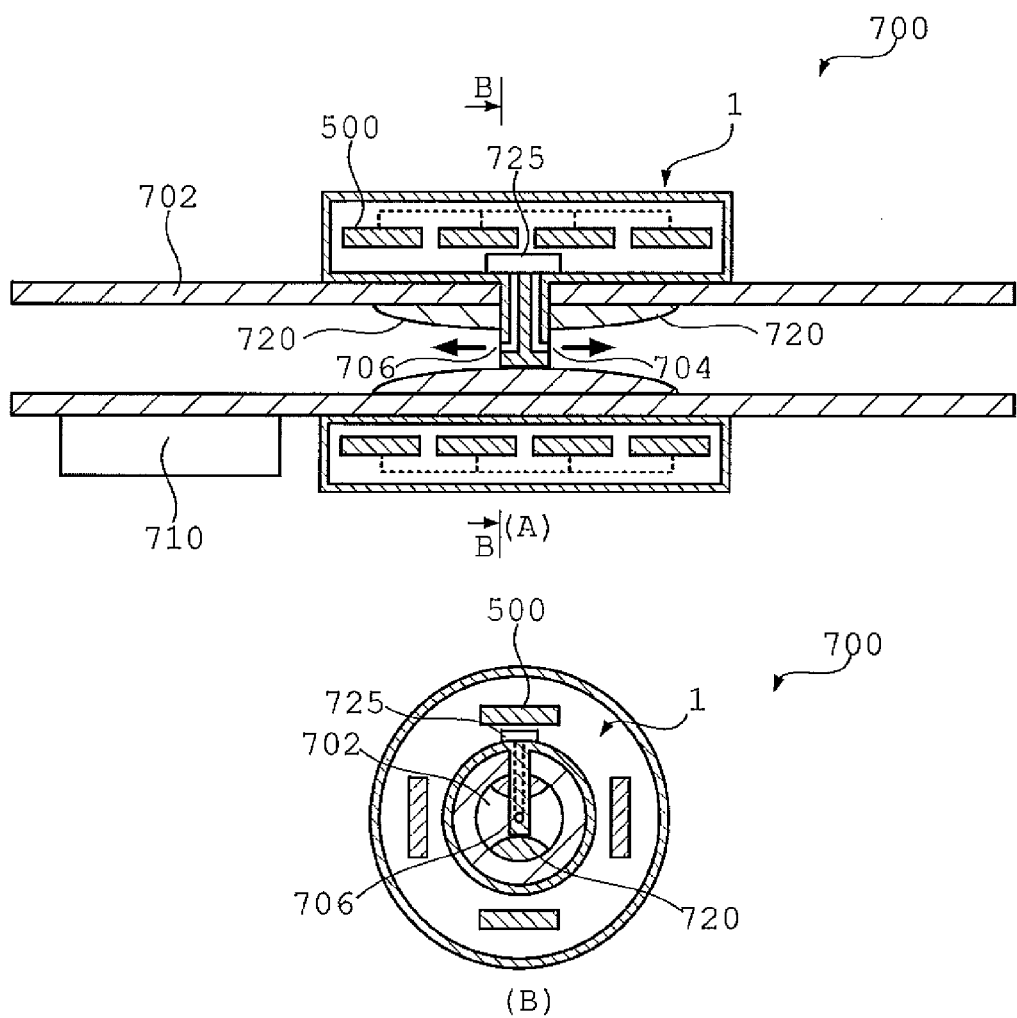
FIG. 14A is a cross-sectional view from the front showing the structure of a breathing assistance device according to a third embodiment of the present invention.
FIG. 14B is a cross-sectional view taken along arrows B-B of FIG. 14A.

In an example of a third embodiment of the invention shown in FIG. 14, the pump unit 1 described in the second embodiment is applied to a breathing assistance device 700 for medical purposes. The breathing assistance device 700 includes a flow path 702 through which a gas for breathing passes, an expiratory nozzle 704 and an inspiratory nozzle 706 placed in the flow path 702 and through which air for acceleration can be discharged in an expiratory direction and an inspiratory direction respectively, the pump unit 1 arranged on the outer surface of the flow path 702 and in the direction of the circumference of the flow path 702, and a battery 710 for driving the pump unit 1. Venturi walls 720 are arranged near the expiratory and inspiratory nozzles 704 and 706 placed in the flow path 702. The battery 710 may be placed in a distant place. Alternatively, a power source line may be connected to omit the battery 710.

Figure 15:
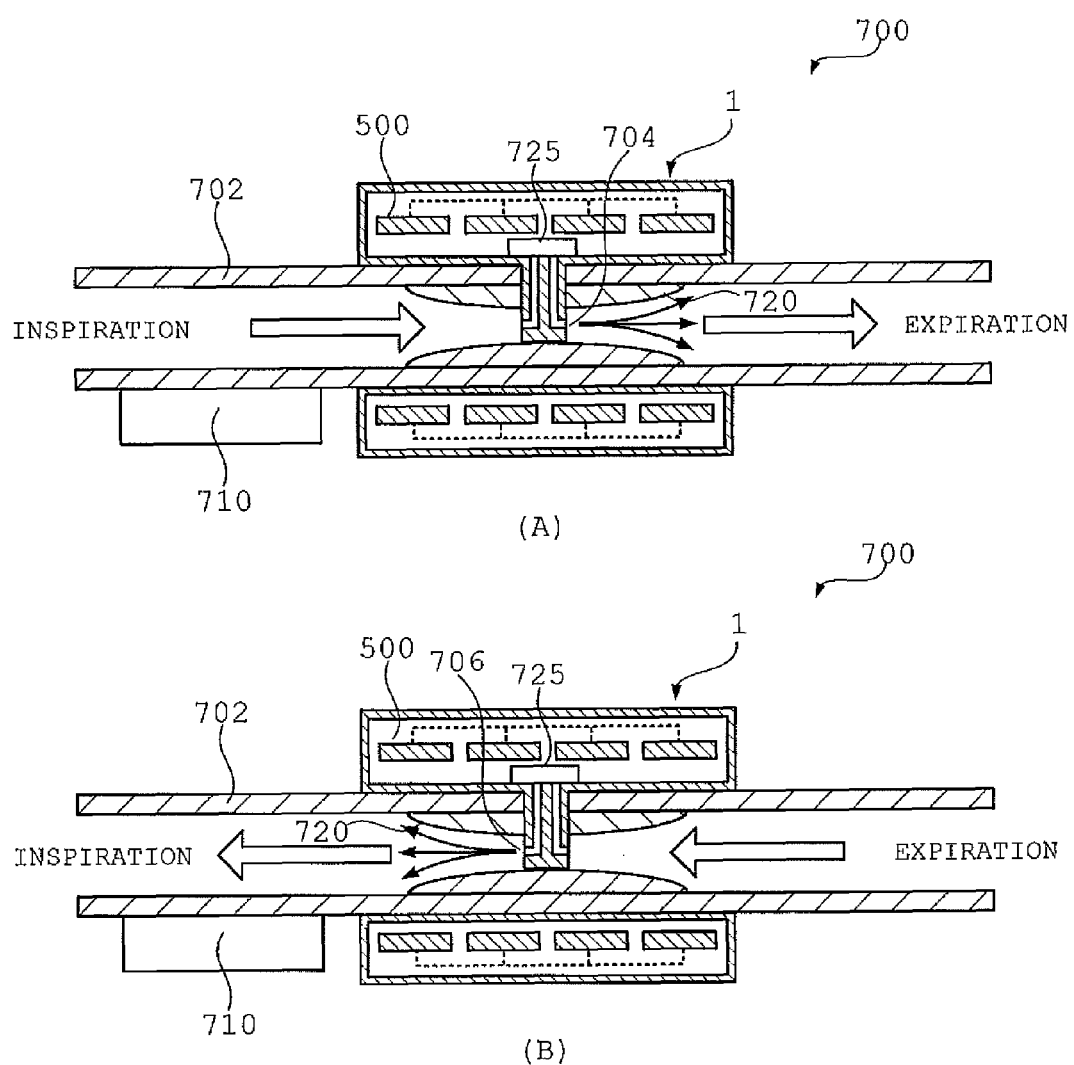
FIGS. 15A and 15B are cross-sectional views showing examples of control of the breathing assistance device.

An integrated discharge port (not shown) placed in the pump unit 1 is provided with an expiration and inspiration switching valve 725. The expiration and inspiration switching valve 725 makes switching between emission of air discharged from the integrated discharge port through the expiratory nozzle 704, and emission of the air through the inspiratory nozzle 706. As shown in FIG. 15, if air is emitted through the expiratory nozzle 704, the emitted air spreads through the venturi wall 720 to place a part responsible for expiration under negative pressure. Then, carbon dioxide emitted from a part responsible for inspiration (lung) is drawn into the air, and the air is caused to flow in the expiratory direction, thereby allowing assistance for expiratory operation. Meanwhile, if air is emitted through the inspiratory nozzle 706 as shown in FIG. 15B, the emitted air spreads through the venturi wall 720 to place the part responsible for inspiration under negative pressure. Then, oxygen supplied from the part responsible for inspiration is drawn into the air, and the air is caused to flow in the expiratory direction (toward the lung), thereby allowing assistance for inspiratory operation.

In the breathing assistance device 700, the downsized pump unit 1 is directly fixed to a pipe itself to form the flow path 702, making it possible to realize the considerably compact size of the breathing assistance device 700. Further, if the flow path 702 moves simultaneously as a user's body moves, the integrated structure of the flow path 702 and the pump unit 1 causes the flow path 702 and the pump unit 1 to move together. This prevents disconnection of the expiratory and inspiratory nozzles 704 and 706 from the pump unit 1, allowing breathing assistance operation of a higher degree of stability and allowing a user to move his or her body easily.

Further, a shortened distance from the pump unit 1 to the expiratory and inspiratory nozzles 704 and 706 can enhance the responsiveness of breathing assistance operation.

Figure 16:
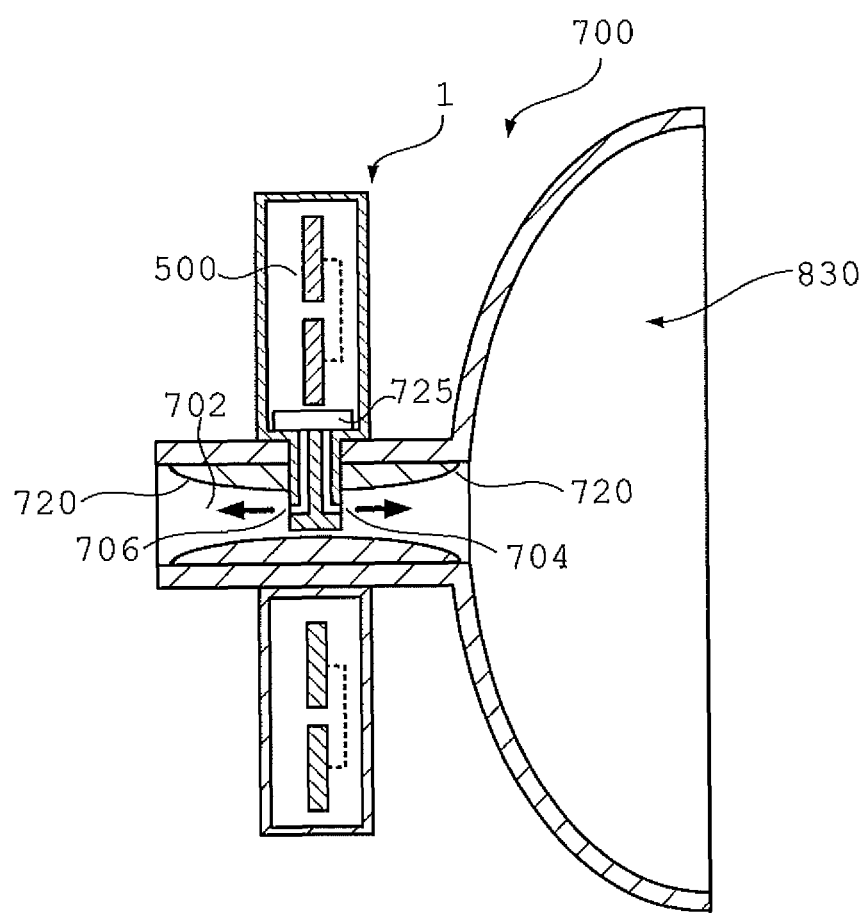
FIG. 16 is a cross-sectional view showing another example of the structure of the breathing assistance device.
Figure 17:
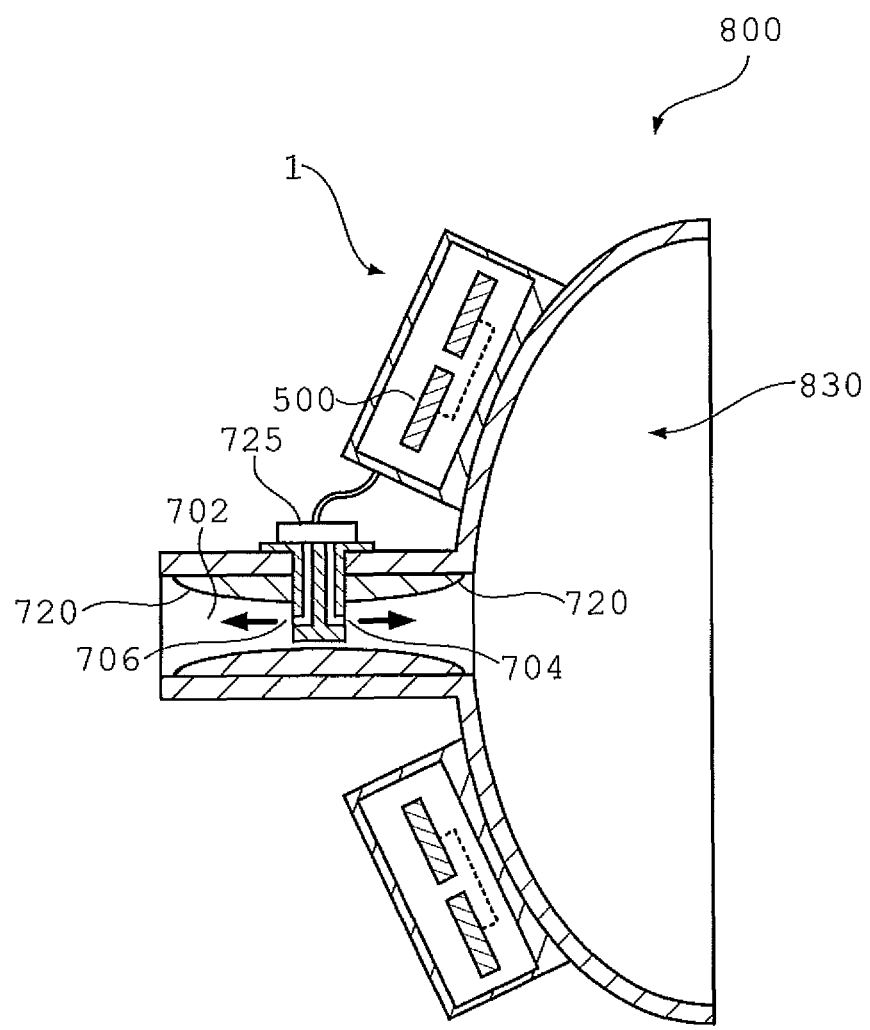
FIG. 17 is a cross-sectional view showing still another example of the structure of the breathing assistance device.
Figure 18:
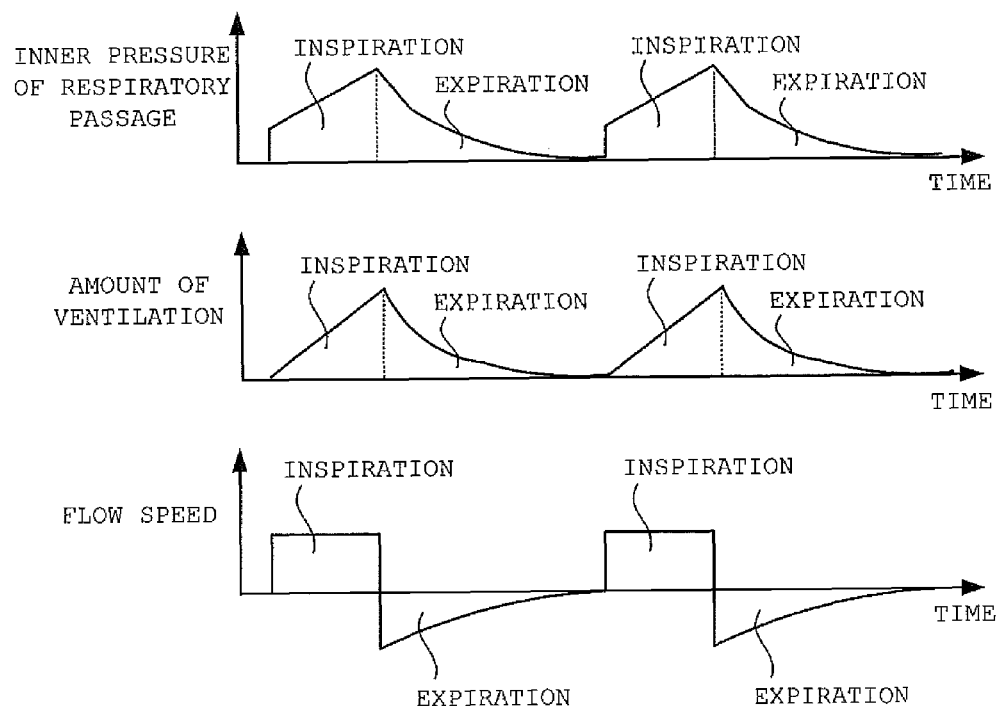
FIG. 18 includes graphs showing examples of control of pressure and a flow rate in a generally used breathing assistance device.

The breathing assistance device 700 can be used while it communicates with an intubation tube inserted from a user's mouth toward a user's trachea. The breathing assistance device 700 can also be used while the flow path 702 is connected to a nasal mask 830 as shown in FIG. 16, for example. For application to a nasal mask, it is preferable that the pump unit 1 be fixed directly on the outer circumference of the nasal mask 830 like in a breathing assistance device 800 shown in FIG. 17, so that it increases entire stability. In the example described here, one pump unit 1 is prepared and supply from the pump unit 1 to an expiratory or inspiratory nozzle is switched by the expiration and inspiration switching valve 725. Meanwhile, two pump units 1 may be prepared, and the pump units 1 may be connected to expiratory and inspiratory nozzles, respectively.

The pump unit and the breathing assistance device of the present invention are not limited to those described in the aforementioned embodiments, but various modifications can certainly be made without departing from the gist of the invention.

The pump unit of the present invention is applicable for various purposes other than a breathing assistance device. Further, the breathing assistance device of the present invention is applicable to assist in breathing of various living organisms.

The entire disclosure of Japanese Patent Application No. 2011-121270 filed on May 31, 2011 including specification, claims, drawings, and summary are incorporated herein by reference in its entirety.

What is claimed is:

1. A pump unit comprising: a plurality of micropumps arranged in a lattice pattern with rows and columns, the micropumps transferring a fluid in a direction along the columns; an integrated discharge port to which a discharge port of at least a micropump arranged in a most downstream row is directly connected, the integrated discharge port receiving the fluid transferred by the micropumps to be discharged finally through the integrated discharge port; a discharge direct-connection path and a discharge direct-connection valve connecting respective discharge ports of the plurality of micropumps in a middle row directly to the integrated discharge port; an intake direct-connection path and an intake direct-connection valve connecting respective intake ports of the plurality of micropumps in the middle row directly to the fluid to be supplied first from an integrated intake port; a series-connection path and a series-connection valve connecting a discharge port of a micropump in an upstream row directly to an intake port of a micropump in a downstream row; and a controller for controlling the discharge direct-connection valve, the intake direct-connection valve, and the series-connection valve, wherein the controller connects a discharge port of a micropump in the upstream row directly to an intake port of a micropump in the downstream row by opening the series-connection valve and closing the intake direct-connection valve to form a multistage connection in a direction of the columns so that a pressure of the fluid increases from the upstream row to the downstream row, thereby bringing the plurality of micropumps in a pressure preferred transfer state, and connects the discharge ports of the micropumps in a plurality of rows directly to the integrated discharge port by opening the discharge direct-connection valve, and connects the intake ports of the micropumps in the plurality of rows directly to the fluid to be supplied first from the integrated intake port by closing the series-connection valve and opening the intake direct-connection valve, so that the micropumps are connected with each other in parallel, thereby bringing the plurality of micropumps in a flow rate preferred transfer state.

2. The pump unit according to claim 1, wherein the number of the micropumps in operation in the downstream row is the same as or smaller than the number of the micropumps in the upstream row in the pressure preferred transfer state.

3. The pump unit according to claim 1, wherein the number of the micropumps arranged in the downstream row is the same as or smaller than the number of the micropumps arranged in the upstream row.

4. The pump unit according to claim 1, wherein the controller causes the flow rate preferred transfer state and the pressure preferred transfer state to exist together, and changes a relationship between a share of rows to be connected to each other in the pressure preferred transfer state and a share of rows to be directly connected to the integrated discharge port in the flow rate preferred transfer state, thereby changing pressure and a flow rate of the fluid being transferred stepwise.

5. The pump unit according to claim 1, wherein the discharge direct-connection valve, the intake direct-connection valve, and the series-connection valve switch connections of all of the plurality of micropumps arranged in the rows at a time.

6. A breathing assistance device, comprising:
a flow path through which an inspiratory gas or an expiratory gas passes;
a nozzle placed in the flow path and through which a gas for acceleration is blown in an expiratory or inspiratory direction; and
the pump unit according to claim 1, the pump unit supplying the gas for acceleration to the nozzle.

7. A pump unit comprising parallel pump units arranged in a plurality of stages and in each of which a plurality of micropumps are arranged in parallel, wherein the pump unit is provided with: a discharge-side confluence space where flows of a fluid discharged from a plurality of micropumps of an upstream parallel pump unit merge together; an intake-side branching space where flows branching off a fluid are supplied to a plurality of micropumps of a downstream parallel pump unit; a series-connection valve for connecting the discharge-side confluence space for the upstream parallel pump unit directly to the intake-side branching space for the downstream parallel pump unit, or breaking a connection therebetween; a discharge direct-connection valve for connecting the discharge-side confluence space for the upstream parallel pump unit directly to an integrated discharge port through which a fluid is discharged finally, or breaking a connection therebetween; and an intake direct-connection valve for connecting the intake-side branching space for the downstream parallel pump unit directly to a fluid to be supplied first, or breaking a connection therebetween, wherein the discharge-side confluence space, the intake-side branching space, the series-connection valve, the discharge direct-connection valve, and the intake direct-connection valve are provided between the upstream parallel pump unit and the downstream parallel pump unit.

8. The pump unit according to claim 7, further comprising a controller for controlling the discharge direct-connection valve, the intake direct-connection valve, and the series-connection valve, and wherein the controller controls switching between a pressure preferred transfer state where the upstream parallel pump unit and the downstream parallel pump unit are connected in series by placing the series-connection valve in a state of forming a direct connection and placing the discharge direct-connection valve and the intake direct-connection valve in a shutoff state, and a flow rate preferred transfer state where the upstream parallel pump unit and the downstream parallel pump unit are connected in parallel by placing the series-connection valve in a shutoff state and placing the discharge direct-connection valve and the intake direct-connection valve in a state of forming a direct connection.

* * * * *